United States Patent [19]

O'Rear, III et al.

[11] Patent Number: 5,503,850

[45] Date of Patent: Apr. 2, 1996

[54] METHOD AND COMPOSITION FOR THE TREATMENT OF THROMBOSIS IN A MAMMAL

[75] Inventors: Edgar A. O'Rear, III; Philip D. Nguyen; Arthur E. Johnson, all of Norman; Eugene S. Patterson; Thomas L. Whitsett, both of Oklahoma City, all of Okla.

[73] Assignee: Research Corporation Technologies, Inc., Tucson, Ariz.

[21] Appl. No.: 352,975

[22] Filed: Dec. 9, 1994

Related U.S. Application Data

[63] Continuation of Ser. No. 970,981, Nov. 3, 1992, abandoned, which is a continuation of Ser. No. 700,085, May 6, 1991, abandoned, which is a continuation of Ser. No. 538,603, Jun. 1, 1990, abandoned, which is a continuation of Ser. No. 353,693, May 17, 1989, abandoned.

[51] Int. Cl.$^6$ ................................................. A61K 9/127
[52] U.S. Cl. ..................... 424/450; 424/94.63; 424/94.64
[58] Field of Search ................................. 424/45, 94.63, 424/94.64; 424/94.63, 94.64

[56] References Cited

U.S. PATENT DOCUMENTS

| | | | |
|---|---|---|---|
| 4,089,801 | 5/1978 | Schneider | 252/316 |
| 4,235,871 | 11/1980 | Papahadjopoulos | 424/19 |
| 4,244,943 | 1/1981 | Yamahira et al. | 424/94 |
| 4,552,760 | 11/1985 | Murakami et al. | 424/450 X |
| 4,568,544 | 2/1986 | Hasegawa et al. | 424/94 |
| 4,615,885 | 10/1986 | Nakagame et al. | 424/450 X |
| 4,640,835 | 2/1987 | Shimizu et al. | 424/94 |
| 4,681,582 | 7/1987 | Yamamoto | 424/450 X |
| 4,762,720 | 8/1988 | Jizomoto | 424/450 |
| 4,808,405 | 2/1989 | Smith et al. | 424/94.3 |
| 4,861,597 | 8/1989 | Kida et al. | 424/450 |
| 5,000,887 | 3/1991 | Tenzel et al. | 424/450 |

FOREIGN PATENT DOCUMENTS

| | | |
|---|---|---|
| 0160266A2 | 11/1985 | European Pat. Off. . |
| 57-4913 | 1/1982 | Japan . |
| 59-222410 | 12/1984 | Japan . |
| 58-222410 | 12/1984 | Japan . |
| 60-155109 | 8/1985 | Japan . |

OTHER PUBLICATIONS

Schmelter et al. Can. J. Pharmaceutical Science 16 , p. 37, 1981.

Marc J. Ostro, Ed., Chapter 1, pp. 27–51, "Liposome Preparation: Methods and Mechanisms" by Deamer, et al., Marcel Dekker, Inc. (1983).

Article: Soeda, Shinji, et al. Biochemical and Biophysical Research Communications pp. 94–100 (1987).

Nguyen et al., "Thrombolysis Using Liposomal-Encapsulated Streptokinase: An In Vitro Study", unpublished.

Nguyen et al., "Liposomal Encapsulation of Streptokinase Accelerates In Vivo Thrombolysis and Reperfusion", unpublished.

Caride et al., "Liposome Accumulation in Regions of Experimental Myocardial Infarction", Science 198: 735–738 (1977).

Mimms, et al. "Phospholipid Vesicle Formation and Transmembrane Protein Incorporation Using Octyl Glucoside", Biochemistry 20: 833–840 (1981).

(List continued on next page.)

*Primary Examiner*—Gollamudi S. Kishore
*Attorney, Agent, or Firm*—Scully, Scott, Murphy & Presser

[57] ABSTRACT

A composition comprising a plurality of microcapsules suitable for parenteral injection into a mammal comprising a plasminogen activator-containing core, and a semi-permeable biocompatible layer surrounding the core permitting controlled release of at least a portion of the plasminogen activator. A method of reducing the time required for reperfusion of an artery containing a thrombus and a method to reduce the standard dosage requirement of a plasminogen activator in a mammal comprising intravenous injection of a composition comprising a plurality of microcapsules comprising a plasminogen activator core surrounded by a controlled release semi-permeable layer.

12 Claims, 2 Drawing Sheets

OTHER PUBLICATIONS

Schmelter et al., "A Preliminary Study of the Association of Urokinase With Liposomes", Canadian Journal of Pharmaceuitical Science 16(10: 37–39 (1981).

Nissen, "Streptokinase Therapy In Acute Myocardial Infarction", Heart and Lung 13(3,: 223–229 (1984).

Turrens et al., "Protection Against Oxygen Toxicity by Intravenous Injection of Liposome–entrapped Catalase and Superoxide Dismutase", The Journal of Clinical Investigation, 73(1): 87–95 (1984).

Feit et al., "Thrombolytic Therapy in Acute Myocardial Infarction", Cardiovascular Reviews and Report 4(3): 426–444 (1983).

Sim et al., "The Effect of Prostaglandin E1 Incorporated in Lipid Microspheres on Thrombus Formation and Thrombus Disaggregation and Its Potential to Target to the Site of Vascular Lesions", Arzneimittel–Forschung 36–2(8): 1206–1209 (1986).

Ostro, "Liposomes", Scientific American pp. 103–111 (1987).

Warltier et al., "A Canine Model of Thrombin–Induced Coronary Artery Thrombosis", The Journal of Pharmacological Methods 18: 305–318 (1987).

Kopia et al., "Coronary Thrombolysis with Intravanous Streptokinase in the Anesthetized Dog: A Dose–Response Study", The Journal of Pharmacology and Experimental Therapeutics 244(3): 956–962 (1988).

Marder et al., "Thrombolytic Therapy: Current Status", parts 1 & 2, The New England Journal of Medicine 318(23): 1512–1520 and 318(24): 1585–1595 (1988).

Schwartz et al., "Intracoronary Thrombolysis in Acute Myocardial Infarction: Duration of Ischemia as a Major Determinant of Late Results After Recanalization", The American Journal of Cardiology 50(5): 933–937 (1982).

Cockins et al., "A Review of Fibrinoloytic Therapy In Acute Myocardial Infarction", The West Virginia Medical Journal 81: 191–194 (1985).

Ganz et al., "The Intravenous Streptokinase in Evolving Acute Myocardial Infarction", The American Journal of Cardiology 53(9): 1209–1216 (1984).

Caride et al., "Liposome Kinetics in Infarcted Canine Myocardium", Journal of Cardiovascular Pharmacology 6(6): 996–1005 (1984).

Poznansky. Pharmacol. Rev. 36, 1984.

Szoka. Ann. Rev. Biophys. Bioeng. 1980 9, p. 467.

Schmelter, Raymond F., "The Association of Urokinase With Liposomes", U.M.I. Dissertation Services, Doctoral Dissertation, 1978.

Marder et al. New Eng. J. Med. 318(2), 1512–1520) 1988.

METHOD AND COMPOSITION FOR THE TREATMENT OF THROMBOSIS IN A MAMMAL

This is a continuation of application(s) Ser. No. 07/970,981 filed Nov. 3, 1992, now abandoned, which is a FWC of Ser. No. 07/700,085 filed May 6, 1991, now abandoned, which is a FWC of Ser. No. 07/538,603 filed Jun. 1, 1990, now abandoned, which is a FWC of Ser. No. 07/353,693 filed May 17, 1989, now abandoned.

FIELD OF THE INVENTION

The present invention generally relates to methods of treatment and pharmaceutical compositions, and more specifically, but not by way of limitation, to compositions and methods for treating thrombotic conditions.

SUMMARY OF THE INVENTION

The present invention comprises a pharmaceutical composition comprising a plurality of microcapsules suitable for parenteral injection into a mammal. The microcapsules comprise a plasminogen activator-containing aqueous core and a biocompatible layer surrounding the core. The layer is semi-permeable which permits controlled release of at least a portion of the core plasminogen activator within the cardiovascular system of a mammal.

The present invention further comprises a method of treating a thrombotic condition in a mammal in need of such therapy comprising parenterally injecting into the mammal a therapeutically effective amount of a pharmaceutical composition. The composition comprises a plurality of microcapsules suitable for parenteral injection into a mammal, each comprising a plasminogen activator-containing aqueous core and a biocompatible layer surrounding the core. The layer is semi-permeable permitting controlled release of at least a portion of the core plasminogen activator within the cardiovascular system of a mammal.

The present invention also comprises a method of reducing the time required for reperfusion of an artery containing a thrombus in a mammal as compared with the reperfusion time of an artery in a mammal administered a composition comprising an equal amount of a plasminogen activator, comprising parenterally injecting into the mammal a therapeutically effective amount of a pharmaceutical composition comprising a plurality of microcapsules suitable for parenteral injection into a mammal, each comprising a plasminogen activator-containing core; and a biocompatible layer surrounding the core, the layer being semi-permeable permitting controlled release of at least a portion of the core plasminogen activator within the cardiovascular system of the mammal.

The present invention further comprises a method of treating a mammal in need of such therapy with a therapeutically effective amount of plasminogen activator wherein the amount of plasminogen activator is reduced from the minimum standard dosage requirement for the mammal as compared with the standard dosage requirement of a free plasminogen activator. The mammal is parenterally injected with a therapeutically effective amount of a pharmaceutical composition comprising a plurality of microcapsules suitable for parenteral injection into a mammal. The microcapsules comprise a plasminogen activator-containing core and a biocompatible layer surrounding the core, the layer being semi-permeable permitting controlled release of at least a portion of the core plasminogen activator within the cardiovascular system of the mammal.

DETAILED DESCRIPTION OF THE PREFERRED EMBODIMENTS

Figure 1A:
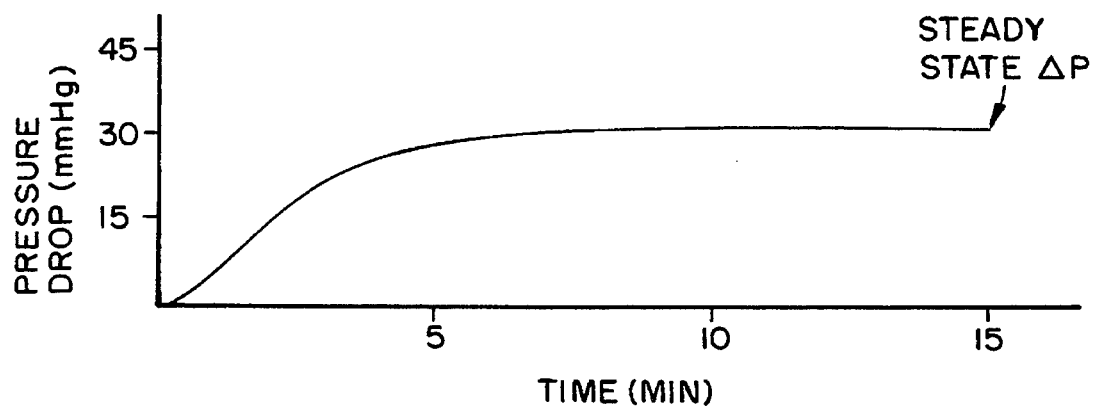
FIG. 1A shows the time dependence of pressure drops monitored during filtration of platelet-poor plasma (PPP) and FIG. 1B shows the time dependence of pressure drops monitored during filtration of streptokinase and platelet-poor plasma mixture (SK/PPP) through the clot-occluded membranes.

The formation of an occlusive thrombus in a vessel can damage tissue normally supplied nutrients by the flow of blood through that vessel. If the occlusive thrombus is formed within an artherosclerotic coronary artery, an acute myocardial infarction may be precipitated which can be fatal to the patient. Although it is desirable to treat any thrombotic condition as soon as possible, there is a marked decrease in mortality, improvement in ventricular function and post-therapeutic quality of life when the myocardial infarction patient is treated rapidly, i.e., within a few hours of the onset of symptoms. Time is of critical importance to acute myocardial infarction patients for two reasons. First, the extent to which the myocardial tissue can be salvaged decreases with time, and second, the rate of recanalization decreases with time because the effectiveness of thrombolysis decays.

In general, thrombolytic therapy is believed to be beneficial to myocardium recovery for a period up to 6 hours. However aggressive intravenous administration of streptokinase has shown a statistically significant different ejection fraction, a measure of cardiac function, for patients treated less than 1.5 hours after the onset of pain compared to patients treated between 1.5 and 4 hours.

Conventional thrombolytic therapy for acute myocardial infarction with plasminogen activators, streptokinase, urokinase, and tPA, requires 30 minutes to 1 hour or longer to reestablish flow; this can mean considerable tissue loss during and following the treatment period. Therefore an acceleration in the thrombolytic activity of a plasminogen activator would be beneficial in treating the myocardial infarction patient. This acceleration is provided by the present invention.

The potential of serious side effects, such as life-threatening uncontrolled bleeding, accompanies the use of plasminogen activators. Reduction of the dosage of the plasminogen activator can reduce the potential for these adverse side effects; this reduction in the minimum effective amount of a plasminogen activator required in a mammal such as a human for thrombolysis is provided by the present invention.

The composition of the present invention comprises a plurality of microcapsules suitable for parenteral injection into a mammal such as a human. The microcapsules comprise a plasminogen activator-containing aqueous core, preferably, a streptokinase-containing core, and a biocompatible layer surrounding the core. The layer is semi-permeable or degradable permitting the controlled release of at least a portion of the core streptokinase within a mammal's cardiovascular system.

Plasminogen activators used in accordance with the present invention comprise streptokinase, urokinase and tPA. "Streptokinase", "urokinase" and "tPA" as described herein include derivatives, conjugates, analogs thereof or agents genetically altered from at least a portion of the genes coding for streptokinase, urokinase or tPA which retain at least a portion of the thrombolytic activity of streptokinase, urokinase or tPA including acylated plasminogen streptokinase activator complex. The plasminogen activators utilized in accordance with the present invention also include any combination of streptokinase, urokinase and/or tPA.

The layer of the microcapsule of the present invention is "biocompatible" which means it is physiologically compatible for the preferred route of administration. For intravenous injection, the osmolality and the pH of the composition is within a range suitable for injection and the microcapsule is sufficiently purified to be as non-antigenic as possible.

The layer of the composition of the present invention is semi-permeable meaning that at least a substantial portion of the plasminogen activator-containing core either passes through the layer or the layer degrades sufficiently with exposure in the cardiovascular system of the mammal such that the plasminogen activator may exert thrombolytic activity on a thrombus within the cardiovascular system of the mammal such as a human. This semi-permeability of the layer permits a controlled release of at least a portion of the core plasminogen activator.

Once injected, the microcapsule circulates within the mammal's cardiovascular system and preferably is site specific for a thrombus therein. Preferably the layer provides a substantial temporary barrier to prevent degradation of the core ingredients by components in the blood and to diminish immunological reactions. At least a portion of the core is released from the microcapsule through the semi-permeable layer in order to dissolve at least a portion of a thrombus in the mammal's cardiovascular system. More preferably, the core is released at or near the thrombus in order to enhance thrombolysis.

The microcapsules of the present invention may be of any size suitable for intravenous injection and capable of having a plasminogen activator-containing core. Preferably the microcapsules are about 250 angstroms to about 10 micrometers.

The layer of the composition of the present invention may comprise phospholipids, and more preferably comprises a liposome. Liposomes are microscopically closed fluid filled vesicles usually comprising phospholipids having hydrophobic tails and hydrophillic heads and can be electrostatically charged or neutral. The liposomes have two standard forms: multilamellar vesicles (MLV) comprising several lipid bilayers and unilamellar vesicles (ULV) comprising a single bilayer surrounding a fluid core. The unilamellar vesicles are characterized as small unilamellar vesicles (SUV) and large unilamellar (LUV).

The LUV are preferred in the present invention although any microcapsule having the appropriate characteristics defined herein may be utilized. Various liposomes can be selected for the desired characteristics or manipulated to produce the desired characteristics. For example, solute retention by liposomes and their half-life in the circulation can be controlled by appropriate manipulation of liposomal membrane fluidity and composition. In the absence of cholesterol, liposomes may leak substantially when introduced intravenously. It is believed this is due to interactions with plasma proteins and to lipid exchange with lipoproteins which can be largely inhibited by the presence of cholesterol. Cholesterol alters the mechanical and structural properties of the phospholipid bilayer of the liposome to cause variable permeability and fragility.

Site selectivity can be controlled to a limited extent by choosing liposomes having variable fragility and/or permeability characteristics: the stresses produced by traversing a partially occluded vessel can open susceptible liposomes thereby selectively delivering the streptokinase to the thrombus site.

It is believed that the liposomes are site specific to thrombi also due to their composition and therefore selectively deliver the plasminogen activator thereto. It is also believed that the liposomes create a temporary barrier which protects degradation of the plasminogen activator by blood components thereby preventing premature inactivation thereof. This may lower the required dosage needed. The temporary barrier provided by the liposome may also diminish or eliminate immunological reactions and the side effect of internal bleeding. However, it is known from the experiments discussed hereafter that encapsulating the plasminogen activator in liposomes permit a controlled release of the plasminogen activator which unexpectedly leads to a marked acceleration of thrombolysis in a mammal when compared to unencapsulated plasminogen activator.

The acceleration of thrombolytic activity can be shown by several factors such as a decrease in the amount of time required to dissolve a thrombus (clot dissolving time (CDT) in example 1 hereafter) or by a decrease in the amount of time required for reperfusion. Using remnant clot size data provided hereafter, the rate of thrombolysis on a 500 mg thrombus can be accelerated from 6 mg/min (using free streptokinase, i.e., unencapsulated streptokinase) to 15 mg/min (using encapsulated streptokinase). In example two, reperfusion time in the canine model was determined by a resolution of electrocardiographic changes induced by ischemia, recovery of left circumflex arterial flow, and the loss of cyanosis wthin the left circumflex coronary artery distribution.

The acceleration of thrombolysis decreases the amount of time required to reperfuse an artery occluded with a thrombus. The rate of acceleration of the present invention is at least 5% faster than the rate of thrombolysis in a mammal administered a composition comprising unencapsulated plasminogen activator.

The composition of the present invention may further comprise a fluid medium suitable for parenteral injection, such as intravenous injection into a mammal, in which the microcapsules are suspended. The carrier should be sterile, have an osmolality and a pH range suitable for injection in a subject, and be relatively inert, i.e., permit the composition to retain at least a portion of the thrombolytic activity. Some examples of suitable carriers are sterile normal saline and sterile dextrose 5% in water and combinations thereof.

The dose of the composition can follow standard dosage requirements, i.e., dosages set by plasminogen activator manufacturers or researchers. For example, in myocardial infarction, a dose of 1.5 million units of streptokinase in solution is infused over 1 hour or 30 units of acylated-plasminogen-streptokinase-activator-complex (APSAC) over 3–5 minutes.

However, the encapsulation of plasminogen activators reduces the minimum therapeutically effective amount of plasminogen activator required to reperfuse an artery occluded by a thrombus by at least 5% as compared with the minimum effective dosage of free plasminogen activator, i.e., plasminogen activator which is not encapsulated. As previously stated, the reduction in the dose of the plasminogen activator can reduce the risk of adverse side effects. Additionally, the cost of the plasminogen activator to is reduced to the patient.

The following examples illustrate the practice of the present invention.

EXAMPLE ONE

In this example, an in vitro study was performed where membrane-bound thrombi were prepared and then used to analyze Streptokinase (SK) and Liposomal Encapsulated Streptokinase (LESK) action in a flow-filtration study. The first step was to ascertain that the microcapsules did not interfere with the filtration test. Therefore, steady state pressure drops were measured for Blank-LUV/PPP and PPP (Platelet Poor Plasma) in their filtrations through the occluded membranes. The pressure drops of the two systems were comparable, indicating that the small liposomes did not alter the resistance to flow of the thrombi, even though some of the liposomes or their lysed membranes might have attached to thrombi occluding the pores. In addition, the results also showed that residual platelets in the PPP did not contribute significantly to a further blockage of the occluded pores.

Figure 2:
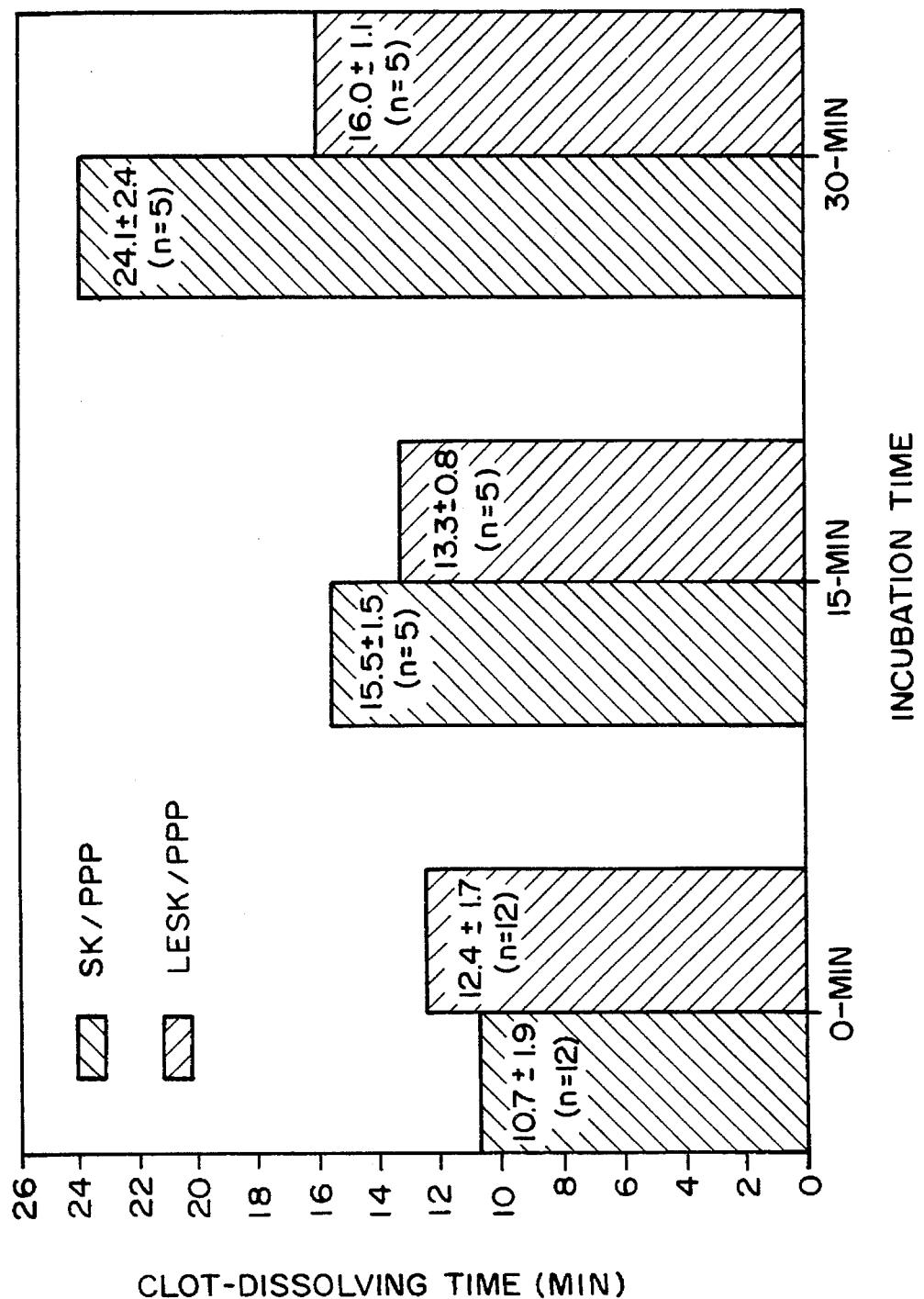
FIG. 2 shows the incubation of streptokinase (SK) and liposomal-encapsulated streptokinase (LESK) in PPP which results in an increase in the clot-dissolving time of membrane-bound thrombi.

When SK was not preincubated with plasma proteins, the clot-dissolving time of LESK/PPP was comparable to that of SK/PPP (FIG. 2). This results indicates that the entrapped SK has similar fibrinolytic ability to that of unentrapped SK at early times. Most important, these data showed that the liposomes were able to release SK at target sites while traversing the occluded pores. The mechanism which releases SK is not known but is probably due to the chemical and physical interactions between the liposomes and their environment.

This example also demonstrates that encapsulating the SK in liposomes can protect the SK from degradation by plasma proteins, as shown by incubating SK and LESK in solutions containing plasma proteins and comparing the results of in vitro thrombolysis.

MATERIALS AND METHODS

Materials

Octylglucoside (OG) (n-octyl-β-D-glucopyranoside) was purchased from Calbiochem (La Jolla, Calif.) and dissolved in Tris-buffered saline (TBS; 20 mM Tris-HCl [pH 7.5], 100 mM NaCl). 1-Palmitoyl-2-oleoyl phosphatidylcholine (PC) was purchased from Avanti Polar-Lipids (Birmingham, Ala.) and used without further purification, while radiolabeled L-α-1-palmitoyl-2-oleoyl-[oleoyl-1-$^{14}$C]phosphatidylcholine ([$^{14}$C]PC) came from New England Nuclear (Boston, Mass.). Triton X-100 was obtained from Research Products International (Mount Prospect, Ill.) and trisodium citrate was acquired from J. T. Baker Chemical (Phillipsburg, N.J.). Streptokinase (SK) (Sigma Chemical, St. Louis, Mo.) solution was prepared fresh by dissolving 10,000 IU (1 vial) of the lyophilized powder in 1 ml of TBS. Dialysis tubing (molecular weight cut off 12,000–14,000) was obtained from Spectrum Medical Industries (Los Angeles, Calif.) and Sepharose CL-6B was purchased from Pharmacia LKB Biotechnology (Piscataway, N.J.). Hydrophilic polycarbonate membranes (Nuclepore Corp., Pleasanton, Calif.) contained 3-μm diameter cylindrical pores at a density of $2 \times 10^6/cm^2$ according to the manufacturer's literature.

Liposome Formation and Streptokinase Encapsulation

The procedures for forming large unilamellar lipid (LUV) vesicles by the detergent removal method have been well documented. Large unilamellar vesicles (LUV) were produced for the purpose of this study as follows. PC (10 mg) in 2 ml of chloroform/methanol (1:1 v/v) in a 10-ml pyrex test tube was evaporated with a stream of nitrogen and lyophilized overnight. The thin film of dried PC coating the bottom of the tube was resuspended in 250 μl of 0.4M OG in TBS by warming at 37° C. for 2 hours with frequent stirring. After the PC had completely dissolved, 1.5 μg of [$^{14}$C]PC (0.1 μCi) was added, and this solution of lipid and detergent was then designated the PC-OG solution. The remainder of the preparation of LESK was carried out in a cold room at 4° C. For dialysis, samples contained, per ml: 50 μl PC-OG solution; 450 μl of 0.4M OG in TBS; and 5000 U of SK in 500 μl of TBS. To prepare protein-free LUV blank samples (Blank-LUV), TBS was added instead of SK solution. This mixture was then dialyzed against 1L of TBS for a total of 48 hours, with dialysate changes after 8 and 24 hours. The dialyzed sample (1 ml or less) was gel filtered at 1 ml/min over Sepharose CL-6B (15 cm×1 cm i.d., pre-equilibrated in TBS) in order to separate LESK from non-encapsulated SK. The elution of LESK and of SK from the column was detected by monitoring absorbance (and light scattering) at 280 nm ($A_{280}$). Vesicles eluted in the void volume, typically within two 0.5 ml fractions that were pooled and designated the LESK sample. These liposomes were stored at 4° C. and utilized within 48 hours. The recovery of phospholipid in the vesicles was assumed to be directly proportional to the recovery of [$^{14}$C]PC in the pooled vesicle fractions (typically 30%).

Vesicle Size

The COULTER® Sub-Micron Particle Analyzer (Model N4MD) was used to determine particle size and size distribution of the liposomes by laser light scattering. The measuring principles are based on the theory of Brownian motion and photon correlation spectroscopy.

SK Activity and Concentration Assays

The activities and concentrations of SK before and after liposomal encapsulation were determined using available commercial kits and their procedures (activity: Helena Laboratories, Beaumont, Tex.; concentration: Bio-Rad, Richmond, Calif.). Standard SK in lyophilized powder was reconstituted with normal saline to give a total activity of 40,000 U/ml, and serially diluted with TBS to create a standard activity curve ranging from 200 to 10,000 U/ml. Before an assay, the entrapped SK was released from liposomes by adding OG to a final concentration of 40 mM; this concentration of OG did not affect the measurement of either SK activity or concentration.

SK Adsorption to or Penetration of Liposome Membranes

To examine the association of SK with the vesicular membrane, 0.5 ml of 10,000 U/ml SK was added to 0.5 ml of Blank-LUV, incubated at 4° C. for 4 hours, and then subjected to gel filtration as described above. Following the chromatography, the liposome fraction was assayed for SK activity and concentration.

Clot Formation

All blood donors (n=16) were healthy, non-smoking male volunteers, who were not on medication and had fasted during the previous 12 hours. Their average age was 25 years. Venous blood was drawn from the arm of the donor into sterile disposable plastic syringes and added to trisodium citrate solution (1.1 ml 3.8% (w/v) citrate/10 ml whole blood) in siliconized test tubes. Platelet-rich plasma (PRP) was obtained by centrifugation of citrated blood at 1000 rpm (145×g) for 10 minutes in a Beckman AccuSpin™ centrifuge (Model ACSR-IM-3, Palo Alto, Calif.). The upper portion (about 2.8 ml) of the supernatant was removed and designated PRP. The remainder was centrifuged at 5000 rpm (3400×g) for another 20 minutes to obtain platelet-poor plasma (PPP). Platelet content in PRP and PPP was determined in duplicate with a hemacytometer using the phase contrast microscopy method as described by Brecher and Cronkite. The number of platelets counted in PPP totaled (16,250±3,230 platelets/$mm^3$ (n=4, P<0.05).

Hydrophilic Nuclepore membranes with 3-µm diameter pore-size were employed in the pore occlusion. Their special features and preparation procedure prior to filtration have been described elsewhere. To occlude pores in a membrane, 4 ml of PRP at room temperature were placed in a 30-ml plastic syringe. 82.5 µl of 0.125M $CaCl_2$ (Sigma Chemical Co.) were added for each ml of plasma in the syringe and the zero time was immediately recorded. The syringe was slightly stirred by hand to ensure good mixing of $Ca^{++}$ within the plasma. A constant volume flow rate of 1.15 ml/min through the membrane was maintained by a Sage-351 infusion pump. The pressure drop (delta P) was monitored as a dependent variable with a Gould Statham pressure transducer (Model P23ID) connected to a Gould DC amplifier/filter (Model 11-4113-01) and was recorded on a chart recorder. The filtration process was stopped when the delta P reached 120-mm Hg, and the occluded filter was then removed from the filter holder. Light suction, using a Pasteur pipette, was applied to remove the extra gel-like clot filling the filter holder before it was disassembled. The occluded membrane was then washed twice with normal saline solution (0.9% [w/v] NaCl) before being installed in a dry, clean filter holder for the next step of the experiment.

Filtrations Through Occluded Membranes

SK or LESK was added to 5 ml of PPP to a final activity of 250 U/ml. Filtrations of SK/PPP or LESK/PPP through occluded membrane-bound thrombi were performed as described above. For control filtrations, occluded membranes were filtered with either PPP or Blank-LUV/PPP. After the occluded membranes were filtered with PPP, Blank-LUV/PPP, SK/PPP or LESK/PPP, the morphology of the remnant clots and the membranes was examined under a microscope (Olympus Research Model BHTU).

Incubation of SK and LESK

To study the effect of incubation with plasma proteins on SK activity, equivalent activities of unencapsulated SK and of LESK were separately injected into siliconized glass tubes containing 5 ml of the same PPP preparation. The contents of each tube were gently mixed for 1 minute with a Hematology Mixer (Fisher Scientific, Pittsburg, Pa.) before incubation at 37° C., and the tubes were slowly inverted three times at 5 minutes intervals thereafter. After either 15 minutes or 30 minutes, the mixture was subjected to filtration with occluded membranes as described earlier.

Data Analysis

All statistical comparisons were analyzed with the Student's t-test. The statistical significance was accepted only when the probability was less than 0.05. Unless indicated otherwise, results are expressed as mean ± SD.

RESULTS

Encapsulation Efficiency of Liposomes

The procedure developed here enabled us to encapsulate 30% of the total SK added to the sample at the beginning of the process (Table 1). The radioactivity measurements show that about ⅓ of the original amount of PC was converted to liposomes (Table 1). The measurements of SK activity and concentration also showed that only a small amount of SK (approximately 2%) was adsorbed to, or penetrated the surface of, Blank-LUV (Table 1). Thus, more than 90%–95% of the SK in the LESK preparation is encapsulated within the vesicles.

Vesicle Size and Distribution

Particle size analysis shows 82 (±3)% (n=5) of the vesicles in the solution have a particle-diameter size of 178 (±40) nm (n=5).

Pressure Drops in Filtrations

Figure 1B:
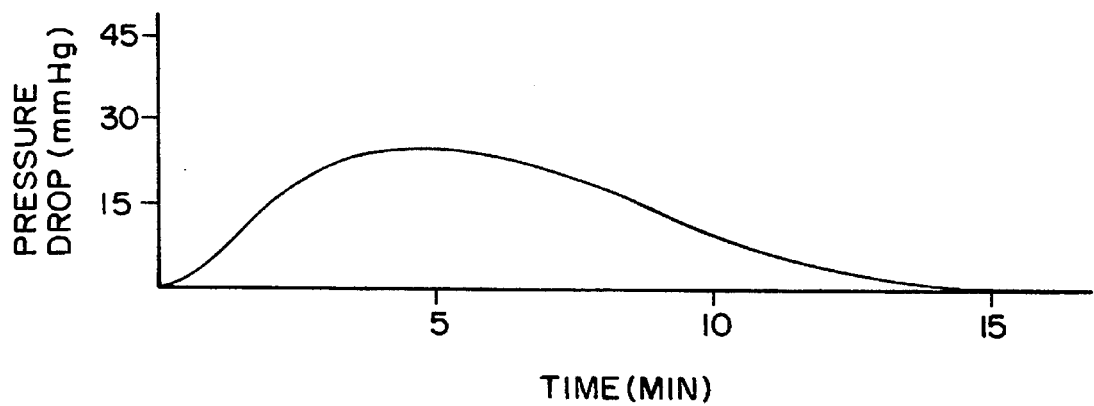

Time-dependent changes in pressure during filtration indicate the extent to which pores are being occluded during filtration with recalcified citrated-PRP or are being reopened during a filtration with SK/PPP or LESK/PPP. The delta P's obtained after 15 minutes of filtration with PPP or Blank-LUV/PPP through occluded membranes were considered as the steady state of delta P's (FIG. 1-*a*). The steady state delta P's in filtrations of Blank-LUVPPP were comparable to those obtained for PPP (i.e., 37.0±7.7 mm Hg (n=12) vs. 35.6±8.6 mm Hg (n=12), respectively). In contrast, a zero or base-line pressure was observed when these solutions were filtered through the non-occluded membranes using the same flow rate as for the case of occluded membranes. This result clearly indicated that flow resistance was due to the presence of thrombi and was not significantly affected by LUV.

Solutions of SK/PPP and of LESK/PPP with the same SK activities were filtered through the occluded membranes in order to compare their clot-dissolving capabilities. The fibrinolytic effect of unencapsulated SK and of LESK was monitored by recording the delta P as a function of time when a solution of SK/PPP or of LESK/PPP was filtered through the occluded membrane (FIG. 1-*b*). For filtrations with these solutions, delta P increased to a maximum, and then decreased gradually to the base-line pressure. The clot-dissolving time (CDT) was taken to be the time between the start of filtration and the time when the delta P returned to the base line. In the absence of preincubation with plasma, the CDT of LESK/PPP [12.4±1.7 min (n=12)] was slightly greater (P<0.05, see FIG. 2) than that of SK/PPP [10.7±1.9 min (n=12)].

A reduction in the fibrinolytic activity of either unencapsulated SK or LESK would result in an increase of CDT, and such a decrease in SK activity was observed when either SK or LESK was incubated with PPP (note increased CDT in FIG. 2). After 15 minutes of incubation, the CDT of SK/PPP increased to 15.5±1.5 minutes (n=5), P<0.05, while the CDT of LESK/PPP increased less, to 13.3±0.8 min (n=5).

After a 30 minute incubation, the CDT of SK/PPP was considerably greater than that of LESK/PPP (24.1±2.5 min, n=5 vs. 16.0±1.1 min, n=5; P<0.05). This result indicated that the unentrapped SK was inactivated during its exposure to plasma proteins, while the entrapped SK is largely protected by the phospholipid bilayer.

Microscopic Study

A microscopic investigation of occluded membranes after being filtered with SK/PPP or LESK/PPP indicated that pores in the membrane were completely cleared from traces of thrombus formation, while those filtered with PPP or Blank-LUV/PPP still showed pores being occluded with large meshes of fibrin and platelet aggregates.

TABLE 1

RECOVERY EFFICIENCY OF LIPOSOMAL ENCAPSULATION

| | Values Before Encapsulation | Values After Gel-filtration (mean ± SD) | Percentage (mean ± SD) | n |
|---|---|---|---|---|
| Phosphatidylcholine (mM)[a] | 2.54 | 0.87 ± 0.18* | 34.3 ± 7.2 | 9 |
| SK Activity (U/ml) | 4942 ± 42 | 1344 ± 240* | 27.2 ± 4.8 | 9 |
| SK Concentration (μM)[b] | 13.1 ± 0.1 | 4.0 ± 0.6* | 30.8 ± 4.3 | 9 |
| Amount of SK Adsorbed to Blank-LUV | | | | |
| SK Activity (U/ml) | 4945 ± 51 | 102 ± 6* | 2.1 ± 0.1 | 5 |
| SK Concentration (μM)[b] | 13.1 ± 0.1 | 0.3 ± 0.01* | 2.3 ± 0.1 | 5 |

[a]Phosphatidylcholine (mol wt = 787)
[b]Streptokinase (mol wt = 50,000).
*P < 0.05 compared to values before encapsulation.

EXAMPLE TWO

Liposomes were prepared as previously described. The observed encapsulation efficiency of SK in liposomes of the zwitterionic lipid 1-palmitoyl-2-oleoyl phosphatidylcholine, as determined by measurements of streptokinase activity and total protein, was about 30%. Extraliposomal streptokinase was then removed from LESK preparations by gel-filtration using Sepharose CL-6B (Pharmacia). Over 92% of the streptokinase in the final LESK suspension resided within the liposomes.

The present study examined the performance of the liposome suspensions in vivo, using a minor modification of an established canine model of myocardial infarction based on a thrombus obstruction. Mongrel dogs of either sex were anesthetized with intravenous sodium pentobarbital (30 mg/kg). An endotracheal tube was inserted and the animals were ventilated with room air using a constant volume respirator. A left thoracotomy was performed in the 4th intercostal space and the heart was exposed. The left circumflex coronary artery was isolated proximal to the first obtuse marginal branch and left circumflex coronary artery flow was measured using a 20 mHz pulsed Doppler or electromagnetic flow probe. Arterial thrombosis was initiated by the injection of 100 U thrombin (Sigma) and 0.1 ml whole blood into a 5–10 mm long segment of proximally and distally ligated left circumflex coronary artery. After 10 minutes, the proximal ligature was released. After an additional 5 minutes, the distal ligature was also released. In some experiments, as many as three injections were necessary to form an occlusion thrombus (Table 2). The thrombus was allowed to mature for 30 minutes before streptokinase administration. At the conclusion of the experiment, the artery was dissected and thrombus mass was determined gravimetrically.

The thrombolytic activity of liposomal encapsulated streptokinase was directly compared to free streptokinase. The relative dosages of the two thrombolytic drugs were identical. An initial bolus of 20,000 U preceded an i.v. infusion of 2000 U/min until recanalization was observed. Similar to reported findings for the left anterior descending coronary artery, the average time required for reperfusion with streptokinase alone was about 78±43 minutes (mean ± standard deviation, see Table 2). Reperfusion was documented by (1) a resolution of electrocardiographic changes induced by ischemia, (2) recovery of left circumflex arterial flow, and (3) the loss of cyanosis within the left circumflex coronary artery distribution. In stark contrast to the values for free streptokinase, the liposomal encapsulated streptokinase greatly reduced thrombolysis times to an average of 32±28 minutes, with some observed reperfusions occurring as quickly as 10 minutes. With the assumptions of normal distributions and of equivalent sample populations, this is a statistically significant difference at P<0.05. Not surprisingly, reperfusion times within each group seemed to correlate with the number of thrombin injections required to form a stable clot.

Liposomal enclosure of the plasminogen activator clearly increased the effectiveness of streptokinase in this canine model, as lower total dosages of the encapsulated material were needed to reestablish blood flow. In these preliminary, unoptimized experiments, average total free streptokinase administered equaled 170,500 U compared to 81,900 U of LESK. Furthermore, the sizes of the remnant thrombi which were isolated from the excised coronary segment confirmed the accelerated thrombolysis, although the data were incomplete (Table 2). The residual clots were smaller in LESK-treated animals, even though the dosages and time of action of LESK were reduced. Most important, encapsulation of SK shortened by more than 50% the time needed for reperfusion.

The mechanism by which liposome encapsulation acts to accelerate thrombolysis in vivo is not clear. As noted above, we suspect that isolating streptokinase in liposomes both reduces its inactivation by plasma proteins (as seen in in vitro experiments) and also retards SK initiation of systemic reactions, and prevents depletion or inactivation of key components of the fibrinolytic system. For example, computer models by our group suggest that present clinical dosages cause rapid formation of streptokinase-plasminogen complex, depletion of free plasminogen available for activation, and hence, low levels of plasmin. According to the model, the slow release of streptokinase from the liposomes would tend to lower the concentration of the complex while raising that of plasmin. This different profile of fibrinolytic components could shift the mechanism of lysis from one of activation of clotbound plasminogen principally to one with an increased role for circulating plasmin. Other possibilities are that the liposomes facilitate delivery of SK to or into the clot by concentrating near the clot and/or by preferentially releasing SK as the vesicles experience flow stress as they pass the thrombus.

Table 3 shows the decrease in the amount of required streptokinase when the streptokinase was encapsulated by the liposome.

Lastly, it is unlikely that the results of these preliminary experiments reflect the greatest possible reduction in reperfusion times. For example, tPA and urokinase exhibit greater binding affinity for fibrin than SK, as well as an enhanced ability to activate clot-bound plasminogen. Consequently, the tPA and urokinase activators may display more rapid thrombolysis, particularly when protected from inactivation within liposomes.

TABLE 2

IN VIVO THROMBOLYSIS EXPERIMENTS
WITH FREE AND ENCAPSULATED STREPTOKINASE

| Dog No. | Number of Thrombin Injections | Reperfusion Time (min) | Thrombus Weight Remaining |
|---|---|---|---|
| Free Streptokinase | | | |
| 1 | 2 | 62 | 5.0 |
| 2 | 3 | 132 | 16.5 |
| 3 | 1 | 27 | — |
| 4 | 3 | 112 | 18 |
| 5 | 1 | 55 | 75 |
| Liposomal Encapsulated Streptokinase | | | |
| 6 | 1 | 10 | 2.6 |
| 7 | 1 | 10 | 0 |
| 8 | 3 | 72 | 10.5 |
| 9 | 2 | 17 | 0 |
| 10 | 3 | 50 | 3.9 |

TABLE 3

IN VIVO THROMBOLYSIS EXPERIMENTS
WITH FREE AND ENCAPSULATED STREPTOKINASE

| Dog No. + | Dosage* (units) |
|---|---|
| Free Streptokinase | |
| 1 | 140,280 |
| 2 | 276,080 |
| 3 | 72,380 |
| 4 | 237,280 |
| 5 | 126,700 |
| Liposomal Encapsulated Streptokinase | |
| 6 | 39,400 |
| 7 | 39,400 |
| 8 | 159,680 |
| 9 | 52,980 |
| 10 | 120,000 |

*Administration of dosage as follows: 2,000 units of streptokinase given as bolus; 2,000 units/minute infused until reperfusion occurred.
+ The average and standard deviation for 5 SK-treated dogs was 18.8 ± 4.0 Kg. and for 5 LESK-treated dogs was 20.9 ± 5.2 Kg.

Changes may be made in the various parts, elements, and steps described herein without departing from the spirit and scope of the invention as defined in the following claims.

What is claimed is:

1. A method of treating a thrombotic condition comprising parenterally administering to a mammal that has a thrombus within a blood vessel, a therapeutically effective amount of a pharmaceutical composition comprising a plurality of large unilamellar vesicles, each of said large unilamellar vesicles encapsulating a plasminogen activator, said large unilamellar vesicles being suitable for parenteral administration to said mammal to deliver the plasminogen activator to said thrombus.

2. The method of claim 1 wherein said mammal is a human.

3. The method of claim 1 wherein said plasminogen activator comprises streptokinase, urokinase, tPA or mixtures thereof.

4. The method of claim 1 wherein said large unilamellar vesicles have neutral charge.

5. A method of reducing the time required for reperfusion of a blood vessel containing thrombus in a mammal comprising parenterally administrating to a mammal that has a thrombus within a blood vessel, a therapeutically effective amount of a pharmaceutical composition comprising a plurality of large unilamellar vesicles, each of said large unilamellar vesicles encapsulating a plasminogen activator, said large unilamellar vesicles being suitable for parenteral administration to said mammal to deliver the plasminogen activator to said thrombus thereby reducing by at least about 50% the time required to reperfuse said blood vessel as compared to the time required using an equivalent amount of said plasminogen activator in free form.

6. The method of claim 5 wherein said mammal is a human.

7. The method of claim 5 wherein said plasminogen activator is streptokinase, urokinase, tPA or mixtures thereof.

8. The method of claim 5 wherein said large unilamellar vesicles have neutral charge.

9. A method of treating a mammal that has a thrombus within a blood vessel, with a reduced amount of plasminogen activator where said plasminogen activator has a predetermined minimum standard dosage requirement in free form comprising parenterally administrating to the mammal a therapeutically effective amount of a pharmaceutical composition comprising a plurality of large unilamellar vesicles, each of said large unilamellar vesicles encapsulating a plasminogen activator, said large unilamellar vesicles being suitable for parenteral administration to a mammal to deliver the plasminogen activator to said thrombus thereby reducing by at least 50% the amount of plasminogen activator required as compared to said predetermined minimum dosage.

10. The method of claim 9 wherein said mammal is a human.

11. The method of claim 9 wherein said plasminogen activator is streptokinase, urokinase, tPA or mixtures thereof.

12. The method of claim 9 wherein said large unilamellar vesicles have neutral charge.

* * * * *

UNITED STATES PATENT AND TRADEMARK OFFICE
CERTIFICATE OF CORRECTION

PATENT NO. : 5,503,850
DATED : April 2, 1996
INVENTOR(S) : Edgar A. O'Rear, et al.

It is certified that error appears in the above-indentified patent and that said Letters Patent is hereby corrected as shown below:

Column 8, line 37: "LUVPPP" should read --LUV/PPP--

Column 11, line 12: after "Remaining" insert --(mg)--

Signed and Sealed this

Twelfth Day of November, 1996

Attest:

BRUCE LEHMAN

*Attesting Officer*     *Commissioner of Patents and Trademarks*